United States Patent
Thiem et al.

(10) Patent No.: US 6,821,072 B2
(45) Date of Patent: Nov. 23, 2004

(54) SYSTEM FOR STAINING AND COVERSLIPPING SPECIMEN SLIDES

(75) Inventors: Stefan Thiem, Heidelberg (DE); Anton Lang, Vienna (AT); Heinz Plank, Neudorf (AT)

(73) Assignee: Leica Microsystems Nussloch GmbH, Nussloch (DE)

( * ) Notice: Subject to any disclaimer, the term of this patent is extended or adjusted under 35 U.S.C. 154(b) by 119 days.

(21) Appl. No.: 10/235,288

(22) Filed: Sep. 5, 2002

(65) Prior Publication Data

US 2003/0049104 A1 Mar. 13, 2003

(30) Foreign Application Priority Data

Sep. 7, 2001 (DE) .......................................... 101 44 042

(51) Int. Cl.[7] .............................................. G01N 33/00
(52) U.S. Cl. ...................... 414/268; 422/65; 435/287.3
(58) Field of Search .................. 422/63, 65; 435/287.3; 414/267, 268, 273

(56) References Cited

U.S. PATENT DOCUMENTS 5,021,218 A * 6/1991 Davis et al. ................. 422/104
2002/0051735 A1 * 5/2002 Dorenkamp et al. .......... 422/65
2004/0002163 A1 * 1/2004 Reinhardt et al. .......... 436/174

FOREIGN PATENT DOCUMENTS

WO    WO 95/20176    7/1995

OTHER PUBLICATIONS

LEICA CV 5000 —The new robotic coverslipper for histology and cytology laboratories, Leica Instruments GmbH, Nussloch, Germany, Dec., 1995.

* cited by examiner

Primary Examiner—Christopher P. Ellis
Assistant Examiner—Mark A. Deuble
(74) Attorney, Agent, or Firm—Hodgson Russ LLP (57) ABSTRACT

A system for staining and coverslipping specimen slides, having a stainer (1) and a coverslipper (3) that are arranged next to one another. A transfer device (2), which transports racks with specimen slides from the stainer (1) to the coverslipper (3), is provided between the stainer (1) and the coverslipper (3). Transport is automated so that operation by the user is substantially reduced.

5 Claims, 6 Drawing Sheets

SYSTEM FOR STAINING AND COVERSLIPPING SPECIMEN SLIDES

CROSS REFERENCE TO RELATED APPLICATIONS

This application claims priority of the German patent application 101 44 042.1 filed Sep. 7, 2001 which is incorporated by reference herein.

FIELD OF THE INVENTION

The invention concerns a system for staining and coverslipping specimen slides. The invention concerns in particular a system for staining and coverslipping specimen slides using a stainer and a coverslipper that are arranged next to one another.

BACKGROUND OF THE INVENTION

WO 95/20176 discloses an instrument for automatic deposition of coverslips. The pickup head possesses suction cups, facing outward from the longitudinal axis of the pickup head, to which a vacuum can be applied individually. A piston that is mechanically preloaded downward with a spring is provided between the suction cups. In order to pick up a coverslip, the pickup head is pressed onto the coverslip stack until the suction cups are in contact with the topmost coverslip. The adhesion between the topmost coverslip and the coverslips below it is overcome by means of a shearing motion. The specimen slides that are to be equipped with coverslips are deposited in a drawer. This does not result in any automation of the apparatus, since the user him—or herself must reload specimen slides.

An automatic stainer and coverslipper are two separate units. According to the existing art, after the staining operation the specimen slides needed to be manually removed from the stainer and inserted into the coverslipper in order to start the process of covering them with coverslips (see Leica brochure CV 5000). Despite the automation of the individual units, manual loading of the coverslipper is necessary. Smooth operation requires that laboratory personnel occupy themselves, at very short intervals of a few minutes, with removing racks from the stainer and loading the coverslipper.

SUMMARY OF THE INVENTION

It is the object of the invention to create a system intended to guarantee handling of specimen slides in as automatic a fashion as possible. The intervention of an operator during staining and subsequent coverslipping of the specimen slides is intended to be minimized.

This object is achieved by means of a system which is characterized in that a transfer device is provided between the stainer and the coverslipper.

BRIEF DESCRIPTION OF THE DRAWINGS

The subject matter of the invention is depicted schematically in the drawings and will be described below with reference to the Figures, in which.

DETAILED DESCRIPTION OF THE INVENTION

Figure 1:
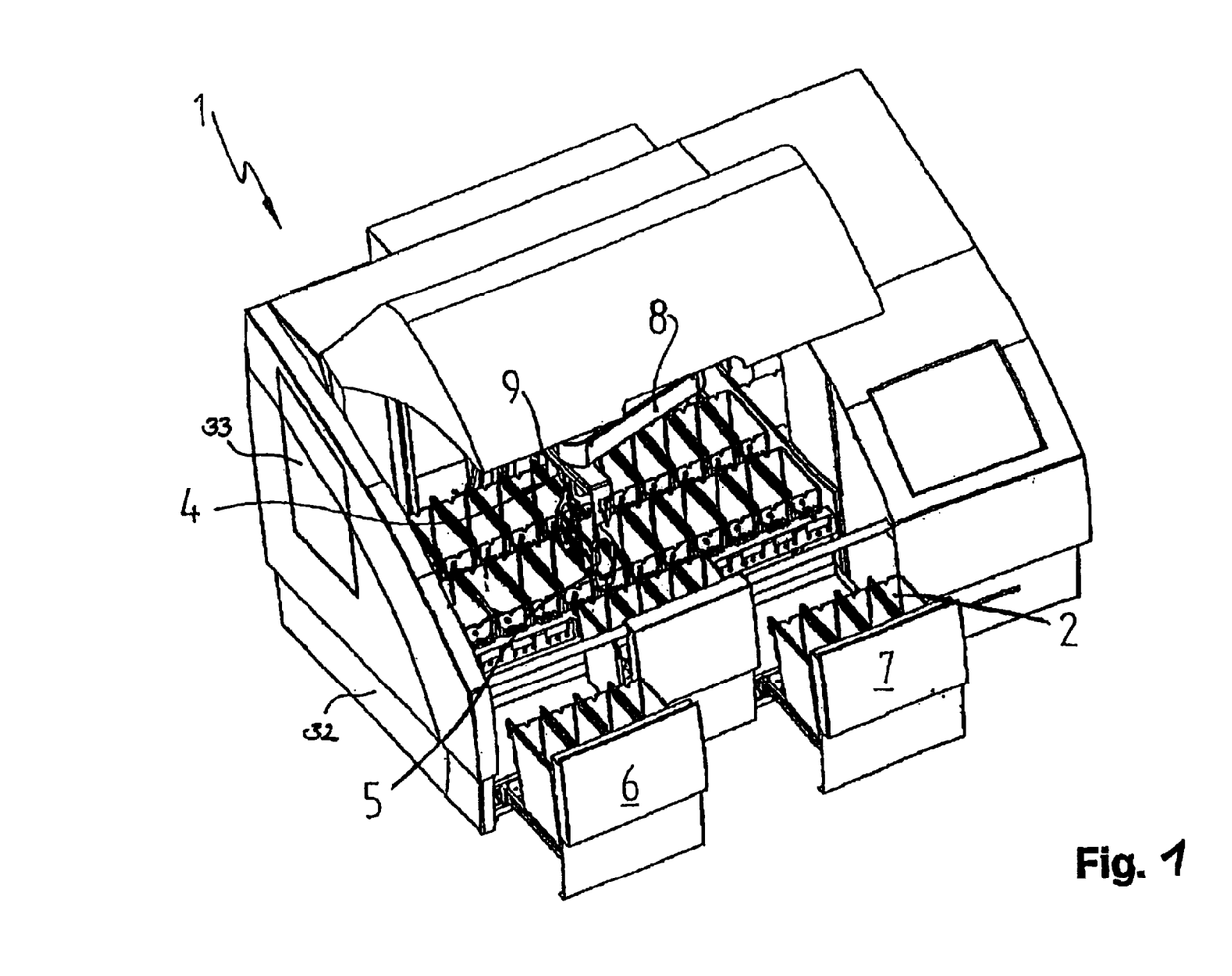
FIG. 1 schematically depicts an exemplary embodiment of a stainer in which the charging station is embodied as a drawer.

It is evident from FIG. 1 that a transport device 4, which conveys specimen slides to the various processing stations 9, is provided in stainer 1. Also provided is a charging station 6 for loading specimens to be treated or racks 5 carrying specimens to be treated. For removing racks 5 from the stainer, a removal station 7 is provided from which racks 5 can be manually conveyed by a user into a downstream element.

Both charging station 6 and removal station 7 are charged by way of transport device 4. The specimen slides present in charging station 6 can thus be removed and delivered to the actual processing stations 9 using transport device 4. After the last processing station 9, racks 5 are conveyed into removal station 7 so that they are (together) removable therefrom. Removal is accomplished once again automatically by way of the transport device, or the specimen slides can be conveyed directly from a processing station 9 into a transfer position 30 (FIG. 3) of the downstream further element of the system. In the exemplary embodiment selected here, transport device 4 is embodied as a robot arm 8. An opening 33, through which racks 5 with specimen slides 5a can be conveyed to a downstream station or into transfer position 30, is configured in a side wall 32 of stainer 1.

Figure 2:
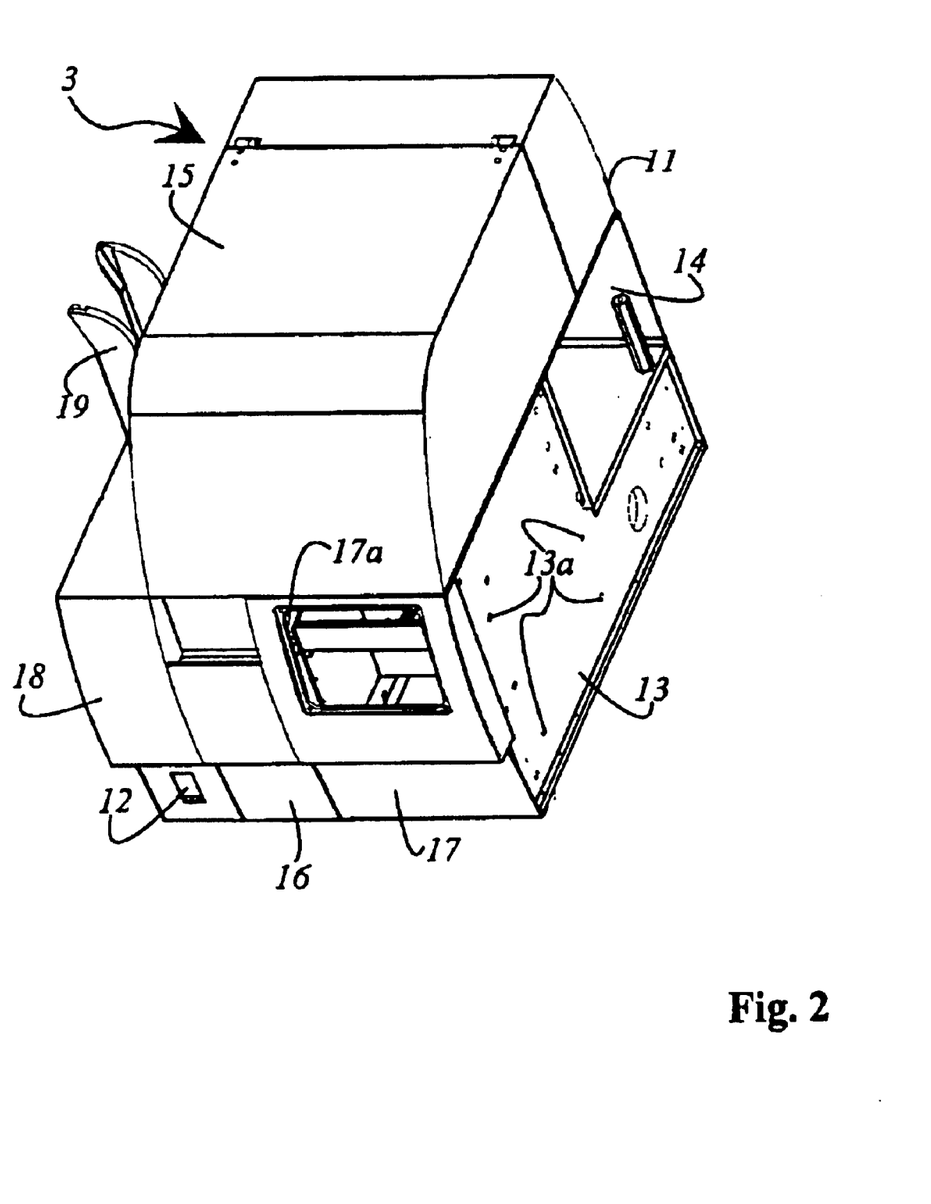
FIG. 2 schematically depicts an exemplary embodiment of a coverslipper.

FIG. 2 schematically depicts an exemplary embodiment of a coverslipper 3. Coverslipper 3 comprises a housing 11 that has on one side wall 13 multiple attachment elements 13a that coact with attachment elements on the corresponding side wall 22 of transfer device 2. Side wall 13 also comprises an opening 14 through which specimen slides are conveyed by transfer device 2 into coverslipper 3. The individual specimen slides are arranged in special racks (not depicted). The interior of coverslipper 3 is covered by a pivotable hood 15. Front wall 16 of the coverslipper comprises a first drawer 17 in which is configured a further opening 17a into which a user interface (not depicted) can be inserted. Provided next to first drawer 17 for the user interface and the access to the electronics of coverslipper 3 is a detachable panel 18 through which the user once again gains access to the interior of coverslipper 3. An output tray 19 for specimen slides equipped with coverslips is also provided on coverslipper 3. Coverslipper 3 can be switched on with a switch 12.

Figure 3:
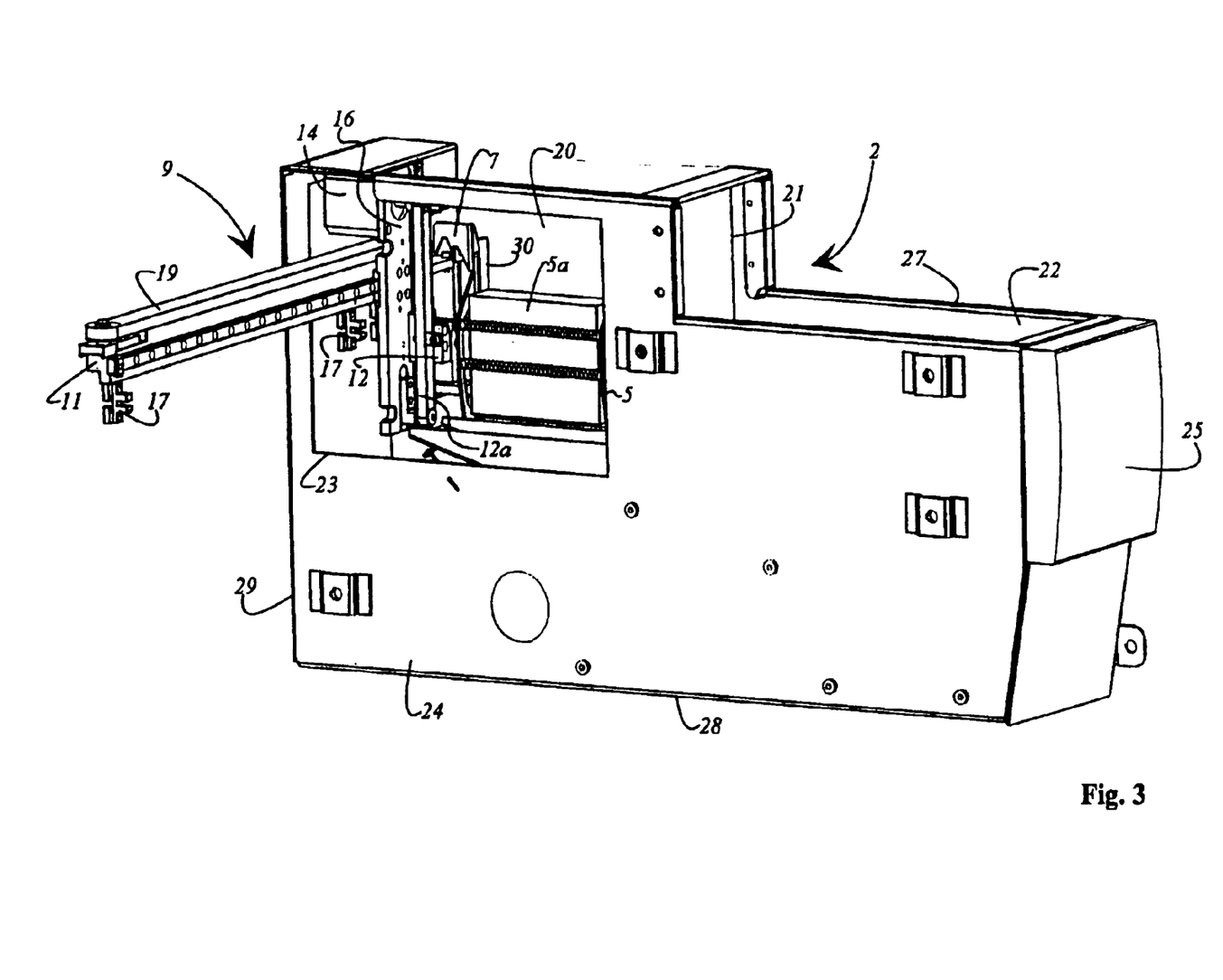
FIG. 3 schematically depicts an exemplary embodiment of a transfer device that transfers specimen slides from the stainer to the coverslipper.

FIG. 3 discloses an element (transfer device 2) of the system according to the present invention that creates communication between stainer 1 and coverslipper 3. Transfer device 2 is provided between stainer 1 and coverslipper 3, and thus connects stainer 1 to coverslipper 3. Transport device 4 of stainer 1 places rack 5 with the stained specimen slides 5a onto a transfer position 30 of transfer device 2. For that purpose, transfer device 2 has a passage 20 that is defined by a cutout 21 in first side wall 22 and a cutout 23 in second side wall 24. Transfer device 2 possesses a front panel 25 through which access to the interior of transfer device 2 is possible. Transfer device 2 is followed by coverslipper 3. Opening 14, in a side wall 13 of coverslipper 3 opposite second side wall 24 of transfer device 2, is configured so that transfer device 2 can transfer racks 5 with specimen slides 5a into coverslipper 3 and can remove racks 5 without specimen slides from coverslipper 3. Communication between coverslipper 3 and stainer 1 occurs as follows: stainer 1 queries whether it can place a rack 5 in coverslipper 3. The response from coverslipper 3 can be "yes" or "no." If "no," the query is repeated at periodic intervals. If "yes," the rack is put in place and a "rack transferred" message is generated. Coverslipper 3 responds "rack received." This procedure eliminates long waiting times for the rack in the transfer position. A quick transfer is advantageous because the specimen slides usually sit in a bath of solvent (often xylene), and wet specimen slides that were just recently stored in solvent exhibit considerably better flow behavior for the coverslip adhesive.

Figure 4:
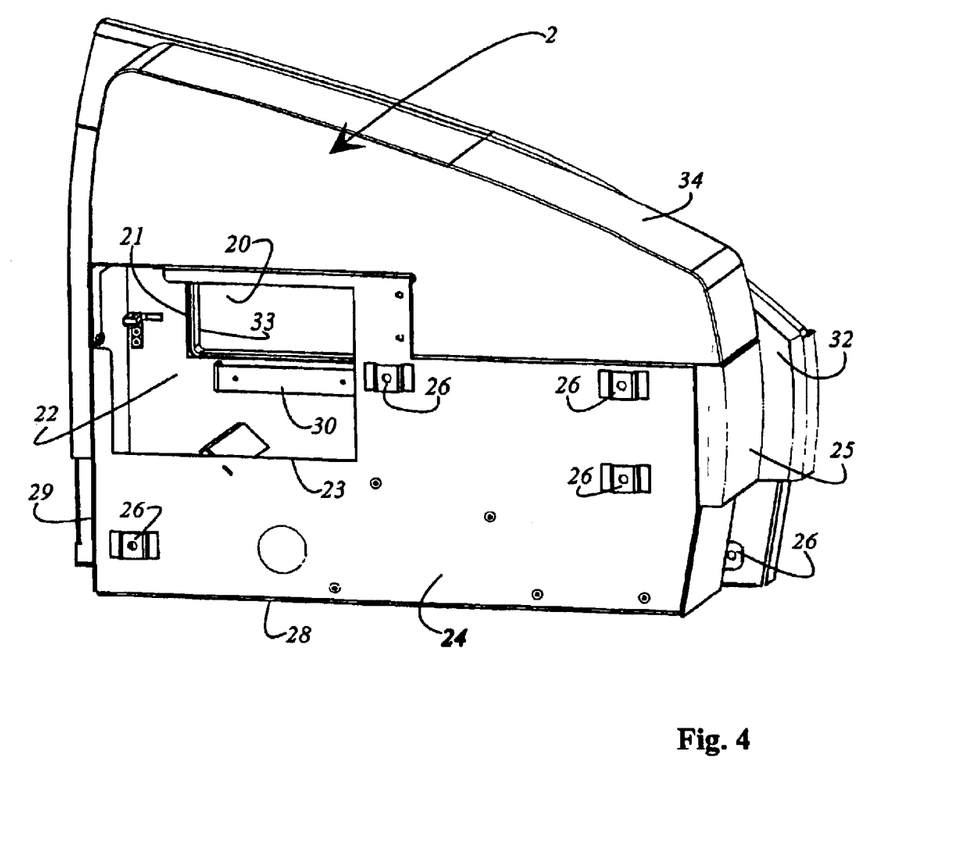
FIG. 4 is a side view in which the transfer device is connected to a side wall of the stainer.

FIG. 4 is a side view of transfer device 2, which is connected to one side wall 32 of stainer 1. For simplicity's sake, only side wall 32 of stainer 1 is depicted. Attachment elements 26, which are provided with corresponding attachment elements (not depicted) on side wall 32 of stainer 1, are again provided on first side wall 22 of transfer device 2. Attachment elements 26, which coact with attachment elements 13a on side wall 13 of coverslipper 3, are also provided in second side wall 24 of transfer device 2. Transfer device 2 comprises a housing 27 that has a bottom 28, a front panel 25, a back wall 29 opposite front panel 25, and the first and the second mutually opposite side wall 22 and 24 already mentioned. Also configured in transfer device 2 is a passage 20 that is defined substantially by a first and a second cutout 21 and 23 in first and second side wall 22 and 24. Transfer position 30 for racks 5 is provided in the region of first cutout 21 in first side wall 22. Cutout 21 in first side wall 22 is arranged opposite an opening 33 in side wall 32 of stainer 1. Through the opening in side wall 32 of stainer 1, racks with specimen slides are transferred out of stainer 1 to the transfer device. The transfer once again occurs through cutout 21 in first side wall 22 of transfer device 2. Transfer device 2 is additionally equipped with a covering hood 34 so as thereby to offer protection against contamination.

Figure 5:
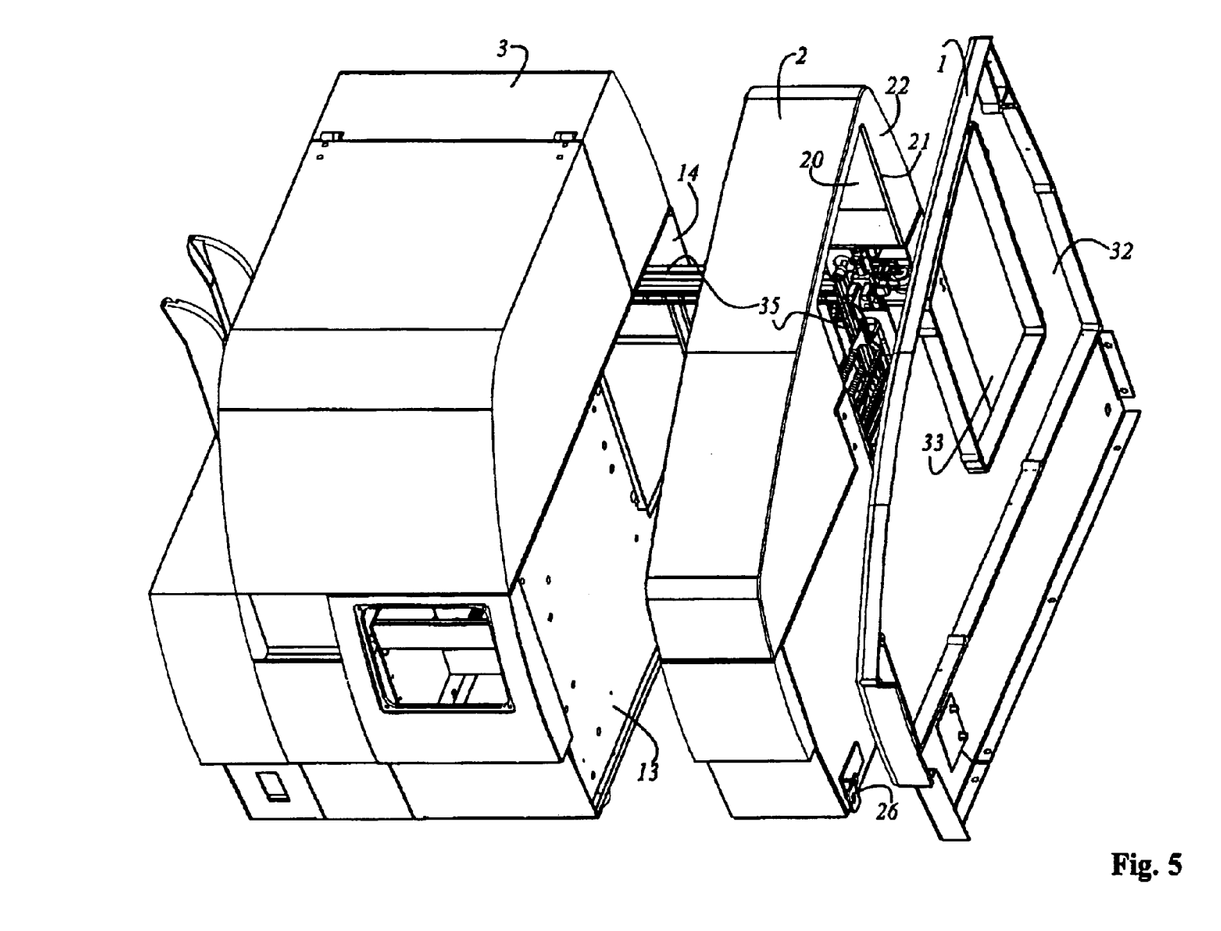
FIG. 5 schematically depicts the system according to the present invention, the individual elements being separated from one another and only one side wall of the stainer being depicted.

As depicted in FIG. 5, the elements of the system are shown separated from one another for better clarity. In operation, stainer 1 (only one side wall 32 shown here), transfer device 2, and coverslipper 3 are connected to one another. Stainer 1 possesses lateral opening 33, through which transport device 4 of the stainer can pass. Specifically, transport device 4 is used on the one hand to accept racks with specimen slides from other processing stations and to transfer racks with specimen slides for transfer to transfer device 2. Transfer device 2 comprises passage 20, which is constituted by a cutout 21 in first side wall 22 and a cutout 23 in second side wall 24. A transport apparatus 35, which passes out through cutout 23 in second side wall 24 and extends into coverslipper 3, is provided in transfer device 2. Transport apparatus 35 extends through opening 14 in side wall 13 of coverslipper 3.

Figure 6:
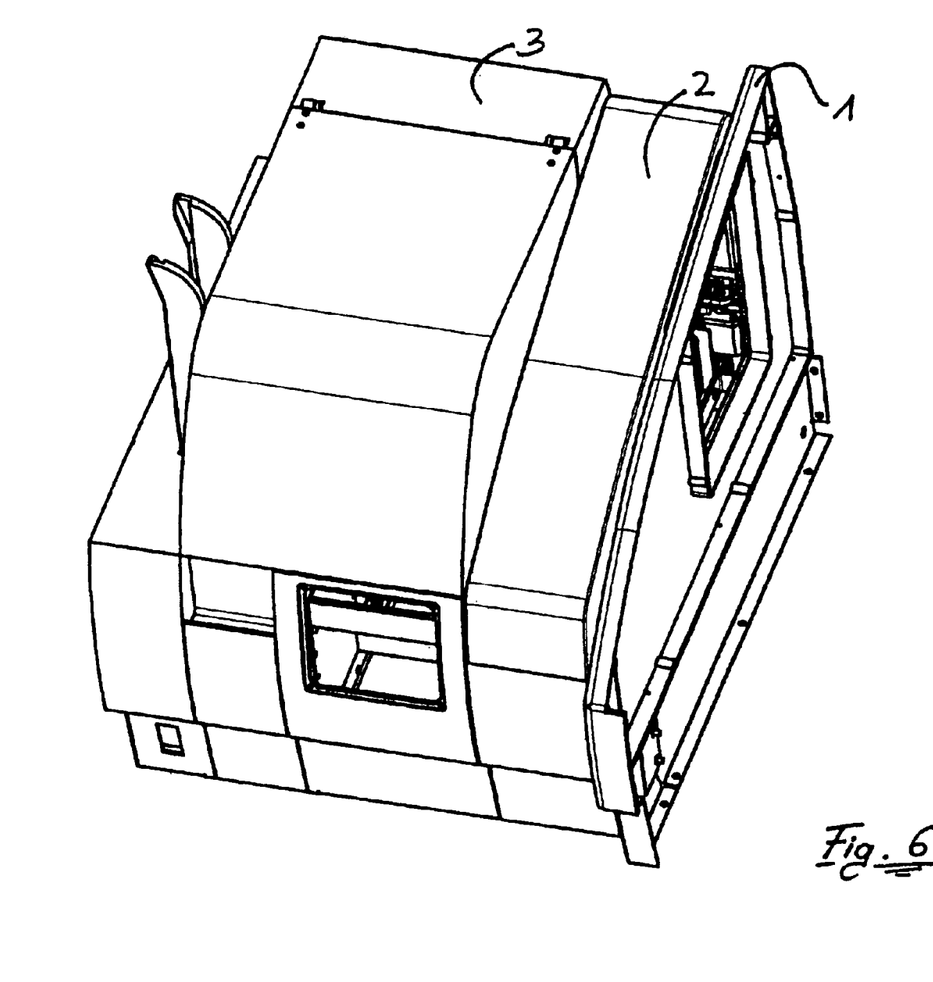
FIG. 6 schematically depicts the system according to the present invention, the individual elements being assembled.

FIG. 6 schematically depicts the system according to the present invention in which the individual elements are assembled. Stainer 1, transfer device 2, and coverslipper 3 are here connected to one another and form a system substantially closed off externally.

The invention has been described with reference to a particular exemplary embodiment. It is nevertheless self-evident that changes and modifications can be made without thereby leaving the range of protection of the claims below.

Parts List

1 Stainer
2 Transfer device
3 Coverslipper
4 Transport device in coverslipper
5 Racks
5a Specimen slides
6 Charging station
7 Removal station
8 Robot arm
9 Processing station
11 Housing
12 Switch
13 Side wall of coverslipper
13a Attachment element
14 Opening
15 Pivotable hood
16 Front wall
17 First drawer
17a Opening
18 Detachable panel
19 Output tray
20 Passage
21 Cutout
22 First side wall
23 Cutout
24 Second side wall
25 Front panel
26 Attachment elements
27 Housing
28 Bottom
29 Back wall
30 Transfer position
32 Side wall of stainer
33 opening
34 Covering hood
35 Transport apparatus

What is claimed is:

1. A system for staining and coverslipping specimen slides, said system comprising:
    a stainer (1);
    a coverslipper (3); and
    a transfer device (2) between said stainer (1) and said coverslipper (3) for transporting said specimen slides from said stainer (1) to said coverslipper (3);
    wherein said transfer device (2) includes a transport device (35) for carrying a rack holding a plurality of said specimen slides, said transport device (35) being configured so that it can extend into said coverslipper (3); and
    wherein said transfer device (2) comprises a housing (27) including a bottom (28), a front panel (25), a back wall (29) opposite the front panel (25), a first side wall (22) having a first cutout (21) therethrough, and a second side wall (24) opposite said first side wall (22) having a second cutout (23) therethrough, said first and second cutouts defining a passage (20) through said housing (27); said housing (27) further including a transfer position (30) for racks near said first cutout (21) in said first side wall (22); and wherein said transport device (35) extends substantially from said transfer position (30) to beyond said second cutout (23) in said second side wall (24).

2. The system as defined in claim 1, wherein said stainer (1) comprises a lateral opening aligned with said first cutout (21) in said first side wall (22) of said transfer device (2); and said coverslipper (3) comprises an opening (33) aligned with said second cutout (23) in said second side wall (24) of said transfer device (2).

3. A system for staining and coverslipping specimen slides, said system comprising:

a stainer (1);

a coverslipper (3); and a transfer device (2) between said stainer (1) and said coverslipper (3) for transporting said specimen slides from said stainer (1) to said coverslipper (3);

wherein said transfer device (2) comprises a first sidewall (22) and a second side wall (24) opposite said first side wall, said stainer (1) comprises a side wall (32) opposite said first side wall (22) of said transfer device (2), said coverslipper (3) comprises a side wail (13) opposite said second side wall (24) of said transfer device (2), said side wall (32) of said stainer (1) and said first side wall (22) of said transfer device (2) include coacting attachment elements (26), and said side wall (13) of said coverslipper (3) and said second side wall (24) of said transfer device (2) include coacting attachment elements (26).

4. The system as defined in claim 1, wherein said front panel (25) of said transfer device (2) is configured as a drawer in order to remove racks deposited by said transfer device (2).

5. A system for staining and coverslipping specimen slides, said system comprising:

a stainer(1);

a coverslipper (3); and a transfer device (2) between said stainer (1) and said coverslipper (3) for transporting said specimen slides from said stainer (1) to said coverslipper (3);

wherein said coverslipper (3) comprises electronics, a first drawer (17) that enables access to said electronics, a detachable panel (18) on a side thereof facing away from said transfer device (2), whereby a user can gain access to an interior of said coverslipper (3).

\* \* \* \* \*

UNITED STATES PATENT AND TRADEMARK OFFICE
CERTIFICATE OF CORRECTION

PATENT NO. : 6,821,072 B2
APPLICATION NO. : 10/235288
DATED : November 23, 2004
INVENTOR(S) : Stefan Thiem et al.

Page 1 of 1

It is certified that error appears in the above-identified patent and that said Letters Patent is hereby corrected as shown below:

Title page, item (73), the assignees should read:
   --Leica Microsystems Nussloch GmbH, Nussloch (DE), and
    Leica Mikrosysteme GmbH, Vienna (AT)--.

Signed and Sealed this

Fifth Day of August, 2008

JON W. DUDAS
*Director of the United States Patent and Trademark Office*